United States Patent
Banerjee et al.

(10) Patent No.: US 11,134,932 B2
(45) Date of Patent: Oct. 5, 2021

(54) SPECIMEN RETRIEVAL DEVICE

(71) Applicant: Covidien LP, Mansfield, MA (US)

(72) Inventors: Saumya Banerjee, Hamden, CT (US); Eric Brown, Haddam, CT (US); Gregory R. Morck, Middletown, CT (US); Roy J. Pilletere, North Haven, CT (US)

(73) Assignee: Covidien LP, Mansfield, MA (US)

( * ) Notice: Subject to any disclaimer, the term of this patent is extended or adjusted under 35 U.S.C. 154(b) by 168 days.

(21) Appl. No.: 16/432,960

(22) Filed: Jun. 6, 2019

(65) Prior Publication Data

US 2020/0046333 A1    Feb. 13, 2020

Related U.S. Application Data

(60) Provisional application No. 62/717,938, filed on Aug. 13, 2018.

(51) Int. Cl.
*A61B 17/00* (2006.01)

(52) U.S. Cl.
CPC .............. *A61B 17/00234* (2013.01); *A61B 2017/00287* (2013.01); *A61B 2017/00367* (2013.01)

(58) Field of Classification Search
CPC ........... A61B 2017/00287; A61B 2017/00367; A61B 17/00234; A61B 2017/00845
See application file for complete search history.

(56) References Cited

U.S. PATENT DOCUMENTS

| | | | |
|---|---|---|---|
| 30,471 | A | 10/1860 | Dudley |
| 35,164 | A | 5/1862 | Logan et al. |
| 156,477 | A | 11/1874 | Bradford |
| 1,609,014 | A | 11/1926 | Dowd |
| 3,800,781 | A | 4/1974 | Zalucki |
| 4,557,255 | A | 12/1985 | Goodman |
| 4,611,594 | A | 9/1986 | Grayhack et al. |
| 4,744,363 | A | 5/1988 | Hasson |
| 4,790,812 | A | 12/1988 | Hawkins, Jr. et al. |
| 4,852,586 | A | 8/1989 | Haines |

(Continued)

FOREIGN PATENT DOCUMENTS

| CN | 1662174 A | 8/2005 |
|---|---|---|
| DE | 3542667 A1 | 6/1986 |

(Continued)

OTHER PUBLICATIONS

Extended European Search Report issued in corresponding European Appl. No. 19191319.3 dated Jun. 23, 2020 (11 pages).

(Continued)

*Primary Examiner* — Sarah A Simpson
(74) *Attorney, Agent, or Firm* — Carter, DeLuca & Farrell LLP (57) ABSTRACT

A specimen retrieval device includes a tubular body, an inner shaft slidably positioned within a longitudinal bore of the tubular body, and a specimen bag supported on the distal portion of the inner shaft. In embodiments, the tubular body tubular body is formed of a lubricious material. The specimen bag is formed from a pattern and welded by a radiofrequency welder. The specimen bag includes a tail section through which the inner shaft passes, and the tail section may be attached to a handle at a proximal portion of the inner shaft.

11 Claims, 8 Drawing Sheets

(56) References Cited

U.S. PATENT DOCUMENTS

| | | |
|---|---|---|
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,016,448 A | 1/2000 | Busacker et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,118,564 B2 | 10/2006 | Ritchie et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |

(56) References Cited

U.S. PATENT DOCUMENTS

| | | |
|---|---|---|
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,525,687 B2 | 9/2013 | Tran |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 10,653,400 B2 * | 5/2020 | Kamaraj .......... A61B 17/00234 |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0113815 A1 | 5/2005 | Ritchie et al. |
| 2005/0116673 A1 | 6/2005 | Carl et al. |
| 2005/0165411 A1 | 7/2005 | Orban |
| 2005/0256425 A1 | 11/2005 | Prusiner |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0035203 A1 | 2/2007 | Bromfield |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0255597 A1 | 10/2008 | Pravong et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0137334 A1 * | 6/2011 | Anderson ............... A61F 2/013 |
| | | 606/200 |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0143211 A1 | 6/2012 | Kishi |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0184536 A1 | 7/2013 | Shibley et al. |
| 2013/0190773 A1 | 7/2013 | Carlson |
| 2013/0193898 A1 | 8/2013 | Williams et al. |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0110453 A1 | 4/2014 | Wingardner et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |
| 2015/0230781 A1 | 8/2015 | Loktionov et al. |
| 2015/0297204 A1 * | 10/2015 | Horton, Jr. ....... A61B 17/00234 |
| | | 606/114 |
| 2017/0049427 A1 | 2/2017 | Do et al. |
| 2017/0215904 A1 | 8/2017 | Wassef et al. |
| 2017/0224321 A1 | 8/2017 | Kessler et al. |
| 2017/0311964 A1 * | 11/2017 | Desai ............... A61B 17/00234 |
| 2017/0325798 A1 | 11/2017 | Prior |

FOREIGN PATENT DOCUMENTS

| | | |
|---|---|---|
| DE | 8435489 U1 | 8/1986 |
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| EP | 2932909 A1 | 10/2015 |
| FR | 1272412 A | 9/1961 |
| GB | 246009 A | 1/1926 |
| JP | H0549647 A | 3/1993 |
| JP | 2008546503 A | 12/2008 |
| WO | 9315675 A1 | 8/1993 |
| WO | 9317630 A1 | 9/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007002180 A2 | 1/2007 |
| WO | 2007048078 A1 | 4/2007 |
| WO | 2007048085 A2 | 4/2007 |
| WO | 2007081601 A2 | 7/2007 |
| WO | 2008114234 A2 | 9/2008 |

(56) References Cited

FOREIGN PATENT DOCUMENTS

| WO | 2009149146 | A1 | 12/2009 |
| WO | 2011090862 | A2 | 7/2011 |
| WO | 2014134285 | A1 | 9/2014 |
| WO | 2015134888 | A1 | 9/2015 |
| WO | 2017189442 | A1 | 11/2017 |

OTHER PUBLICATIONS

European Search Report EP 12191639.9 dated Feb. 20, 2013.
European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.
European Search Report dated Feb. 12, 2019 issued in EP Application No. 18208634.
International Search Report issued in Appl. No. PCT/US2018/058609 dated Feb. 22, 2019.
European Search Report dated Jul. 21, 2015, issued in European Application No. 14 19 9657.
European Office Action corresponing to counterpart Int'l Appln. No. EP 14 19 9657.9 dated Jul. 9, 2016.
CN Office Action dated Jul. 4, 2018 in corresponding CN Patent Application No. 201410855808.8 together with English translation.
Japanese Office Action dated Aug. 27, 2018 in corresponding Japanese Patent Application No. 2014-264805, with English translation.

\* cited by examiner

SPECIMEN RETRIEVAL DEVICE

CROSS-REFERENCE TO RELATED APPLICATION

This application claims the benefit of and priority to U.S. Provisional Patent Application No. 62/717,938 filed Aug. 13, 2018, the entire disclosure of which is incorporated by reference herein.

TECHNICAL FIELD

The present disclosure relates generally to surgical apparatuses for use in minimally invasive surgical procedures, such as endoscopic and/or laparoscopic procedures, and more particularly, the present disclosure relates to a surgical apparatus including a specimen retrieval device for collecting body tissue(s) and/or body fluid(s) during these procedures.

BACKGROUND

Minimally invasive surgery, such as endoscopic surgery, reduces the invasiveness of surgical procedures. Endoscopic surgery involves surgery through body walls, for example, viewing and/or operating on the ovaries, uterus, gall bladder, bowels, kidneys, appendix, etc. There are many common endoscopic surgical procedures, including arthroscopy, laparoscopy, gastroentroscopy and laryngobronchoscopy, just to name a few. In these procedures, trocars are utilized for creating incisions through which the endoscopic surgery is performed. Trocar tubes or cannula devices are extended into and left in place in the abdominal wall to provide access for endoscopic surgical tools. A camera or endoscope is inserted through a trocar tube to permit the visual inspection and magnification of a body cavity. The surgeon can then perform diagnostic and/or therapeutic procedures at the surgical site with the aid of specialized instrumentation, such as forceps, graspers, cutters, applicators, and the like, which are designed to fit through additional cannulas.

When removing certain tissues from the body cavity, for example tumor tissue, it is important that the tumor tissue does not come into contact with healthy or uninvolved tissue. If tumor tissue or tissue parts have to be removed, they may be introduced into an "extraction bag," also referred to herein as a "specimen bag," at the site where the tumor or diseased tissue has been detached from the surrounding tissue, after which the specimen bag is withdrawn from the body, thereby minimizing contact of the diseased tissue with healthy tissue.

Improved specimen bags for use in minimally invasive surgical procedures remain desirable.

SUMMARY

The present disclosure is directed to surgical apparatuses and methods for their use in minimally invasive surgery. In embodiments, the present disclosure provides a specimen retrieval device including a tubular body defining a longitudinal bore, the tubular body having a proximal portion, a distal portion, and a hand grip supported on the proximal portion of the tubular body. The specimen retrieval device also includes an inner shaft having a proximal portion, a distal portion, an actuation handle supported on the proximal portion of the inner shaft, and a support member extending from a distal portion of the inner shaft. The specimen retrieval device also includes a specimen bag supported on the support member at the distal portion of the inner shaft, the specimen bag including an open end, a body, and a tail portion having a longitudinal bore through which the inner shaft passes. The inner shaft is movable in relation to the tubular body from a non-actuated position in which the specimen bag is positioned in a non-deployed state within the longitudinal bore of the tubular body, to an actuated position in which the specimen bag is positioned in a deployed state externally of the distal portion of the tubular body.

In embodiments, a proximal portion of the tail portion of the specimen bag has a hole, and the actuation handle includes a post which passes through the hole at the proximal portion of the tail portion of the specimen bag.

In some embodiments the post is chamfered.

In other embodiments, the support member includes a pair of resilient fingers which support the specimen bag and open the open end of the specimen bag in the deployed state.

In some embodiments, the resilient fingers are positioned adjacent the open end of the specimen bag to open the specimen bag when the specimen retrieval device is in the deployed state.

In embodiments, the tubular body is formed of a lubricious material.

In some embodiments the tubular body is formed of a polymeric material combined with a lubricious material.

In other embodiments, the lubricious material includes hydrophilic polymers, siloxanes, polycarbonates, urethanes, parylenes, or combinations thereof.

In some embodiments, the lubricious material includes a siloxane selected from polydimethylsiloxanes, hexamethyldisiloxanes, polyester-modified methylphenyl polysiloxanes, or combinations thereof.

In other embodiments, the tubular body is formed of a combination of a siloxane and a polycarbonate.

In embodiments, the tail of the specimen bag includes a reinforcement tab.

Methods of the present disclosure also include methods for forming the specimen bag. In embodiments, the method includes cutting a fabric to form a pattern having a body portion and flaps that may be folded and attached to the body portion of the pattern to form a specimen bag. The method also includes cutting holes along the periphery of the pattern; placing the pattern on a radiofrequency welder and locating the pattern in the proper position with the holes along the periphery of the pattern; folding at least some of the flaps of the pattern and attaching them to the body portion of the pattern with the radiofrequency welder to form a channel at a mouth of the specimen bag; placing a reinforcement tab at a proximal portion of the pattern; and folding a flap at the proximal portion of the pattern and attaching it to the body portion of the pattern with the radiofrequency welder to form a tail section of the specimen bag. The tail section thus includes the reinforcement tab sandwiched between the flap and the body portion of the pattern. The method also includes folding a last flap at a distal portion of the pattern and attaching it to the body portion of the pattern with the radiofrequency welder to form a body of the specimen bag.

In some embodiments, the method further includes placing a suture within the channel at the mouth of the specimen bag.

BRIEF DESCRIPTION OF THE DRAWINGS

Various embodiments of the presently disclosed specimen retrieval device are described herein below with reference to the drawings, wherein.

DETAILED DESCRIPTION OF EMBODIMENTS

The present disclosure provides a specimen retrieval device for use in minimally invasive surgical procedures. As used herein with reference to the present disclosure, minimally invasive surgical procedures encompass laparoscopic procedures, arthroscopic procedures, and endoscopic procedures, and refer to procedures utilizing scopes or similar devices having relatively narrow operating portions capable of insertion through a small incision in the skin.

The aspects of the present disclosure may be modified for use with various methods for retrieving tissue specimens during minimally invasive surgical procedures, sometimes referred to herein as minimally invasive procedures. Examples of minimally invasive procedures include, for example, cholecystectomies, appendectomies, nephrectomies, colectomies, splenectomies, and the like.

The presently disclosed specimen retrieval device will now be described in detail with reference to the drawings in which like reference numerals designate identical or corresponding elements in each of the several views. In this description, the term "proximal" is used generally to refer to that portion of the device that is closer to a clinician, while the term "distal" is used generally to refer to that portion of the device that is farther from the clinician. The term "clinician" is used generally to refer to medical personnel including doctors, surgeons, nurses, and support personnel.

Figure 1:
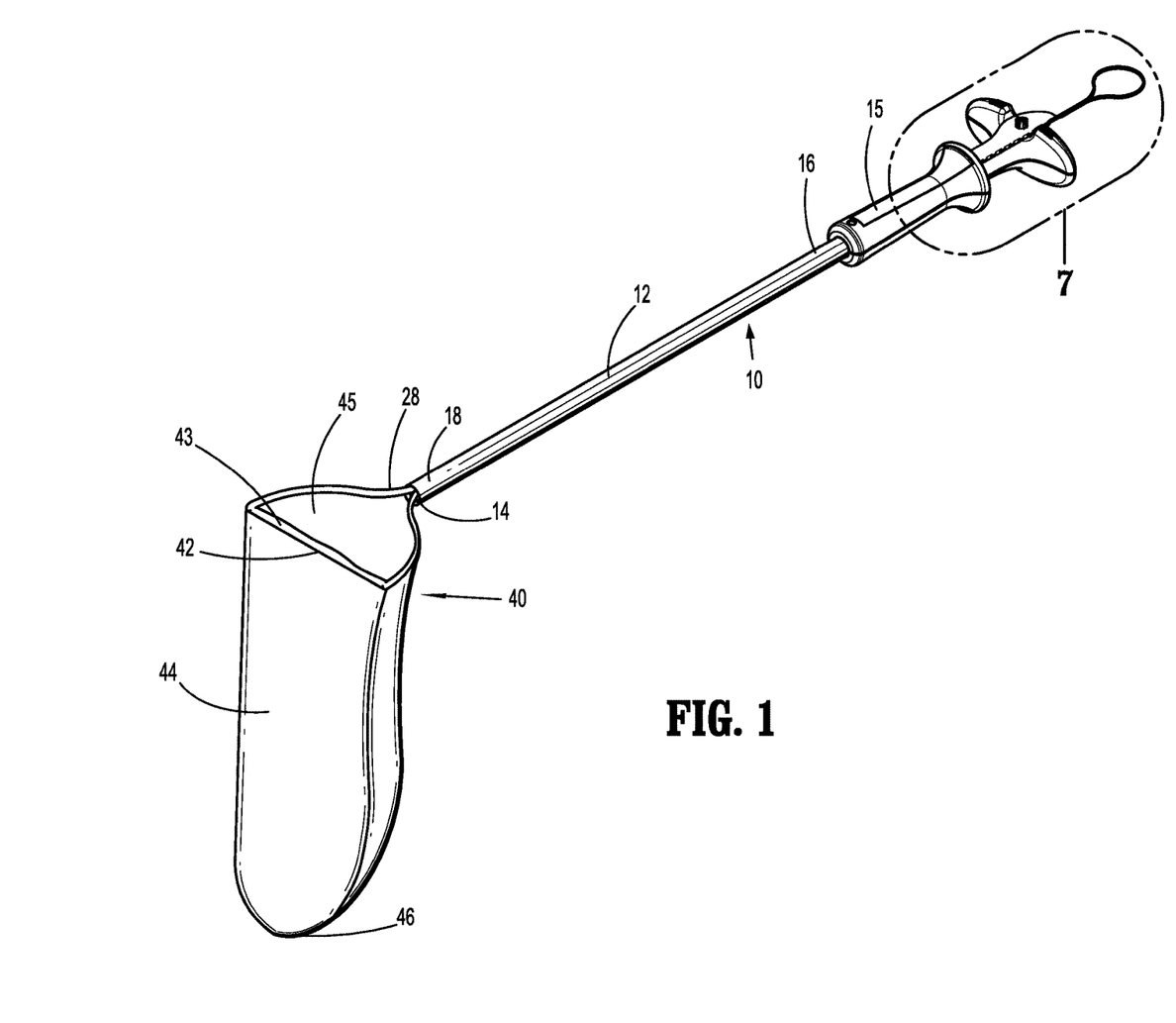
FIG. 1 is a side perspective view of an exemplary embodiment of the presently disclosed specimen retrieval device in a deployed state.
Figure 2:
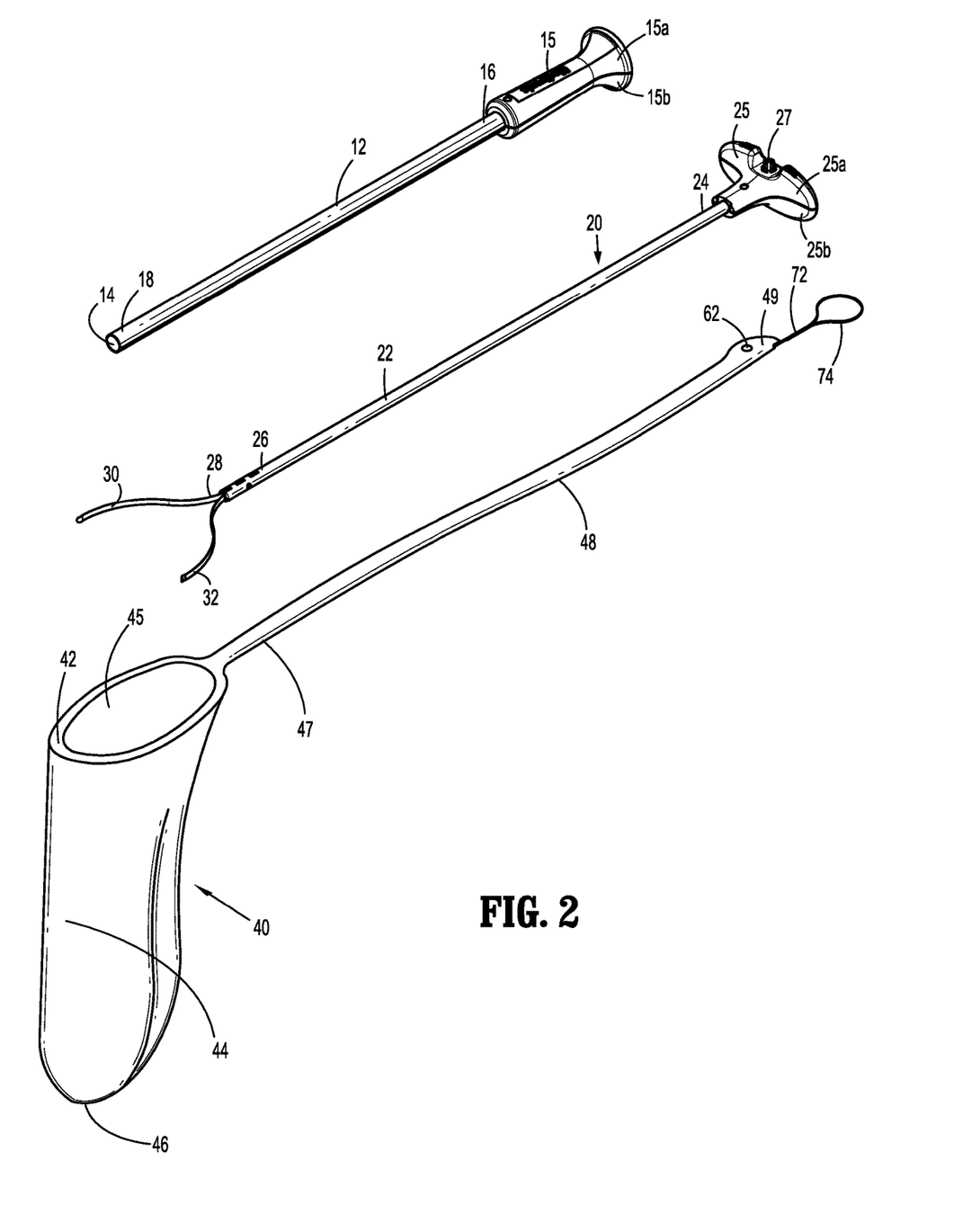
FIG. 2 is an exploded view of the specimen retrieval device shown in FIG. 1.

Referring to FIGS. 1-12, and initially with reference to FIGS. 1 and 2, the specimen retrieval device 10 of the present disclosure includes a tubular body 12 having a proximal portion 16 and a distal portion 18, and defining a longitudinal bore 14 that extends between the proximal portion 16 and the distal portion 18. The proximal portion of the tubular body 12 supports a hand grip 15. The specimen retrieval device 10 also includes an inner shaft assembly 20 (FIG. 6) including an inner shaft 22 slidably positioned within the longitudinal bore 14 of the tubular body 12, an actuation handle 25 secured to a proximal portion 24 of the inner shaft 22, and a specimen bag 40 (FIG. 1) supported on a distal portion 26 of the inner shaft 22.

Figure 6:
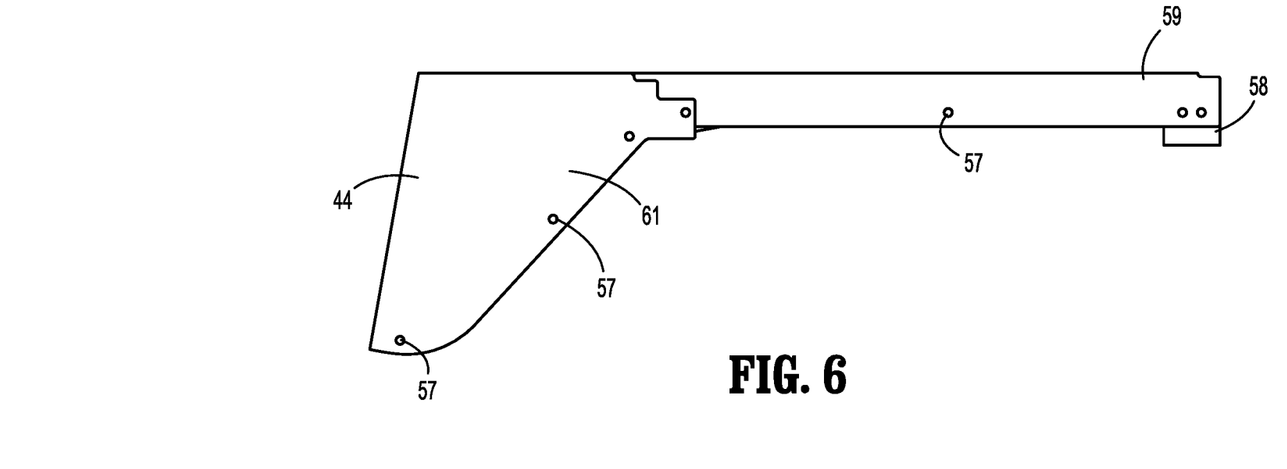
FIG. 6 is a side view of the pattern for forming a specimen bag shown in FIG. 4, showing folding of additional portions of the pattern to produce additional features of the specimen bag.

The hand grip 15 on the tubular body 12 may be formed as a unitary component or, as depicted in FIG. 6, as two separate half components 15a, 15b, that are coupled to one another about the tubular body 12 by one or more suitable coupling methods (e.g., one or more suitable adhesives). In the latter instance, an indent/detent configuration (not shown) may be utilized to facilitate coupling the two separate half components 15a, 15b to one another.

The actuation handle 25 on the inner shaft 22 may likewise be formed as a unitary component or, in embodiments, as depicted in FIG. 6, as two separate half components 25a, 25b that are coupled to one another by one or more suitable coupling methods (e.g., one or more suitable adhesives).

The specimen bag 40 includes a body 44 having a generally tubular or elongated configuration that is defined by an openable and closable portion (or mouth) 42 and a closed portion 46 (FIG. 1). The closable portion 42 defines an opening 45. In some embodiments, the specimen bag 40 includes a tail 48 (FIG. 2) having a neck region 47. Alternatively, other specimen bag configurations are envisioned.

The body 44 of the specimen bag 40 may be made from any suitable biocompatible material (e.g., nylon, urethane, ripstop nylon or latex) capable of forming a flexible collapsible member, or membrane. In embodiments, the material from which the specimen bag is made is resilient, antistatic, pyrogen-free, non-toxic, and sterilizable. The specimen bag 40 may be opaque or clear. In some embodiments, the body 44 of the specimen bag 40 is formed of a nylon material, or combinations of nylon materials. As described in greater detail below, in some embodiments portions of the specimen bag 40 are made of two different nylons that are secured together to form areas of the specimen bag 40 having high strength. In some embodiments, the first nylon material is a 30 denier ("30D") polyurethane coated rip-stop nylon; and the second nylon material is a 1000 denier ("1000D") polyurethane coated nylon.

Turning to FIGS. 3-6, methods for forming the specimen bag of the present disclosure will be described. In embodiments, the specimen bag 40 (FIG. 1) is made using a radio-frequency ("RF") welding process that does not require additional reinforcement at the seams (e.g., sutures, interface materials, etc.). As depicted in FIGS. 3-6, the fabric used to form the specimen bag 40 of the present disclosure is cut to form a pattern 50, with holes 57 along a periphery of the pattern 50. Any means within the purview of those skilled in the art may be used to cut the fabric to form the pattern 50. The holes 57 assist in placement of the pattern 50 on an RF welder (not shown) used to form the specimen bag 40.

Once the pattern 50 has been cut from the fabric, the pattern 50 is placed onto the radiofrequency (RF) welder and located using the holes 57 running along the periphery of the pattern 50 (not shown).

Figure 3:
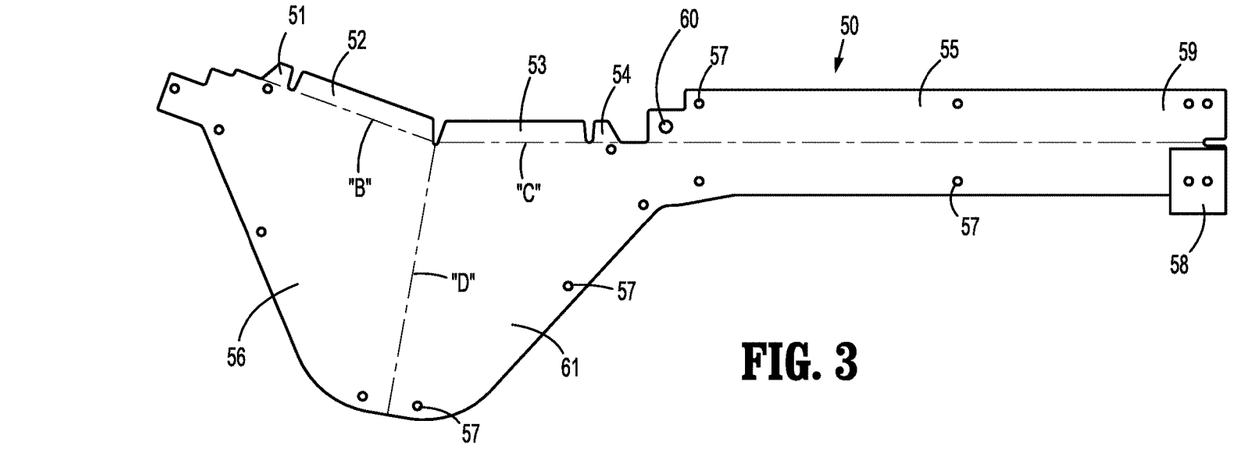
FIG. 3 is a side view of a pattern suitable for forming a specimen bag of the specimen retrieval device of the present disclosure.

After forming the pattern 50 used to form the specimen bag 40, the pattern 50 has various portions that may be folded to form the specimen bag 40, including flaps 51, 52, 53, 54, 55, and 56 (FIG. 3).

Figure 4:
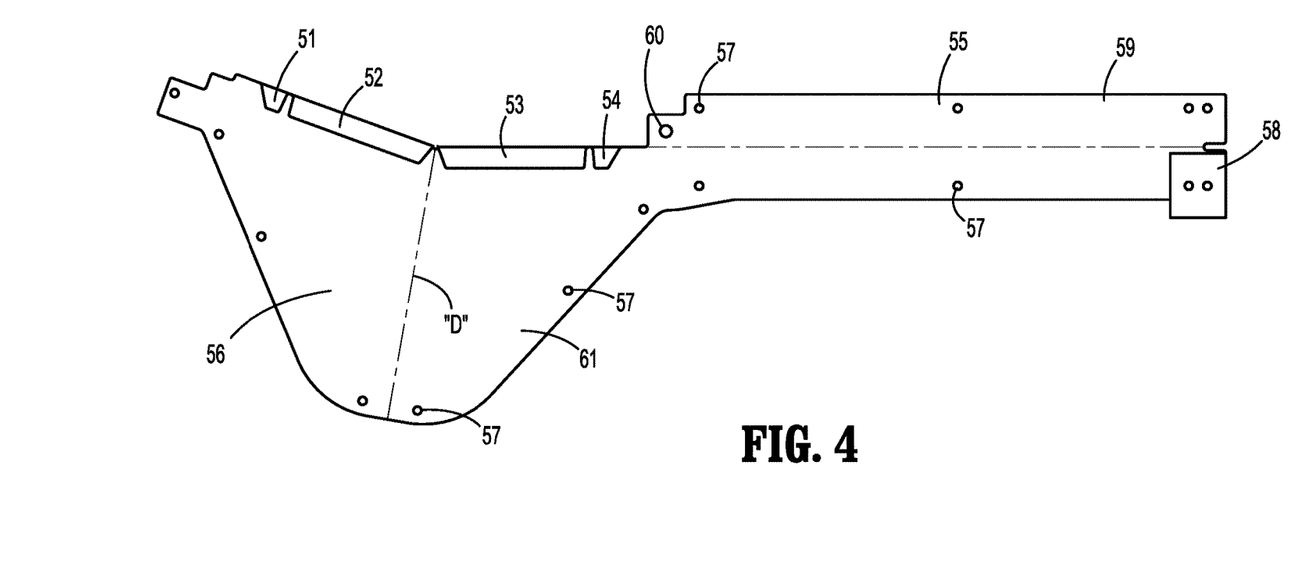
FIG. 4 is a side view of the pattern for forming a specimen bag shown in FIG. 2, showing folding of portions of the pattern to produce features of the specimen bag.

Once positioned on the RF welder, the flaps 51, 52, 53 and 54 are folded over along lines "B" and "C" (FIG. 3) and welded to the fabric (FIG. 4), to form a channel 43 at the mouth 42 of the specimen bag 40 (FIG. 1). The channel 43 may include a suture therein (not shown), which may be used to close the mouth 42 of the specimen bag 40. The flap 55 may then be folded along line "C" (FIGS. 3 and 4) at the proximal portion 59 of the pattern 50 to form a tail section 49 of the specimen bag 40 (FIG. 4).

As shown in FIG. 2, a reinforcement tab 58 may be placed at the proximal portion 59 of the pattern 50 and flap 55 is folded along line "C" so that the reinforcement tab 58 is sandwiched between the fabric as the flap 50 is folded over and attached to the body 61 of the pattern 50. In embodiments, the reinforcement tab 58 is formed of 1000D nylon sandwiched between the 30D fabric used to form the pattern 50. The reinforcement tab 58: adds strength to the 30D material and also acts as a retention feature to prevent the specimen bag 40 from cinching during initial retraction; aids in placement of the specimen bag 40 on the inner shaft 22 and removal of the specimen bag 40 from the body and/or the inner shaft 22 of the specimen retrieval device 10; prevents the tail 48 from ripping without the need for additional suture reinforcement during retraction; and acts as an indicator of the overall device orientation (with respect to location of mouth 42 of the specimen bag 40) for ease of insertion of a tissue specimen into the specimen bag 40 (not shown).

Figure 5:
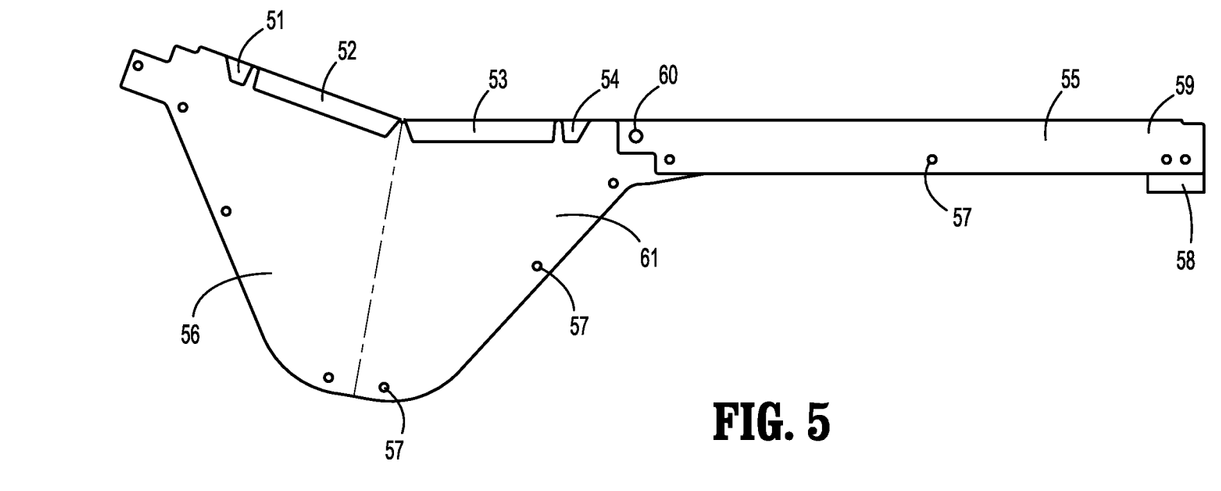
FIG. 5 is a side view of the pattern for forming a specimen bag shown in FIG. 3, showing folding of additional portions of the pattern to produce additional features of the specimen bag.

Once folded, flaps 51, 52, 53, 54 and 55 are secured by RF welding. The flap 56 is then folded along line "D" and welded with the RF welder to form the body 44 of the specimen bag 40 (FIG. 5).

The pattern 50 includes a through-hole 60 on flap 55 that allows the RF welder to secure multiple layers of fabric together (not shown), including welding the flap 56 to the pattern 50 through the through-hole 60 on flap 55 at the neck region 47 of the tail 48. This reinforces the neck region 47, which will experience loads during specimen removal.

The radio-frequency (RF) welding process does not necessitate additional reinforcement via suturing and/or interface materials to bolster the bag seams (found in commercially available products). This combination of the RF welding process and the selection of materials used to form the specimen bag 40 creates a strong, leak proof bag for specimen containment and removal.

As shown in FIG. 6, the specimen bag 40 has a body 44 and a tail 48 that the inner shaft 22 passes through.

Figure 7:
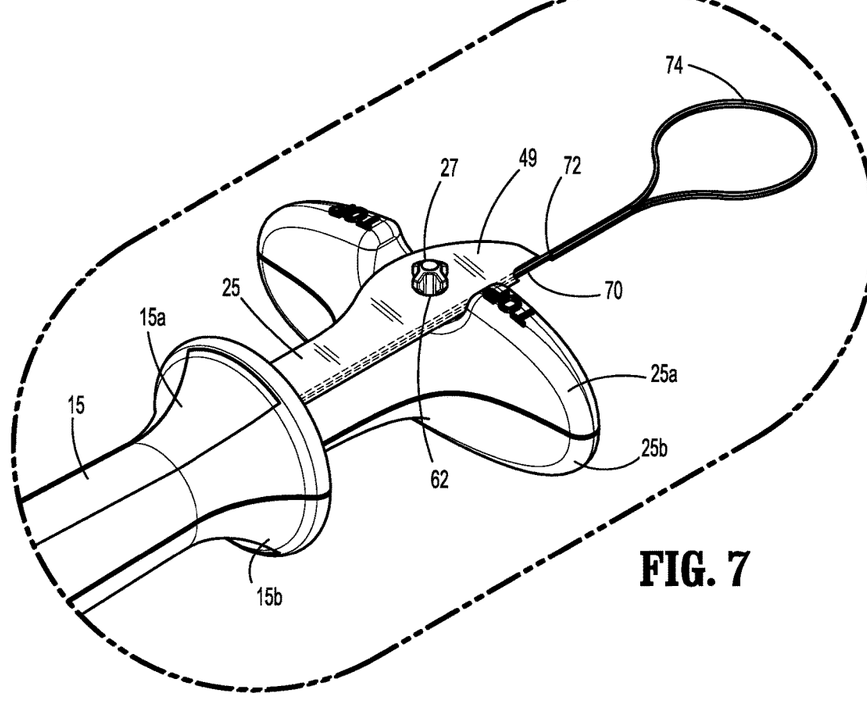
FIG. 7 is an enlarged view of the indicated area of detail shown in FIG. 1.
Figure 8:
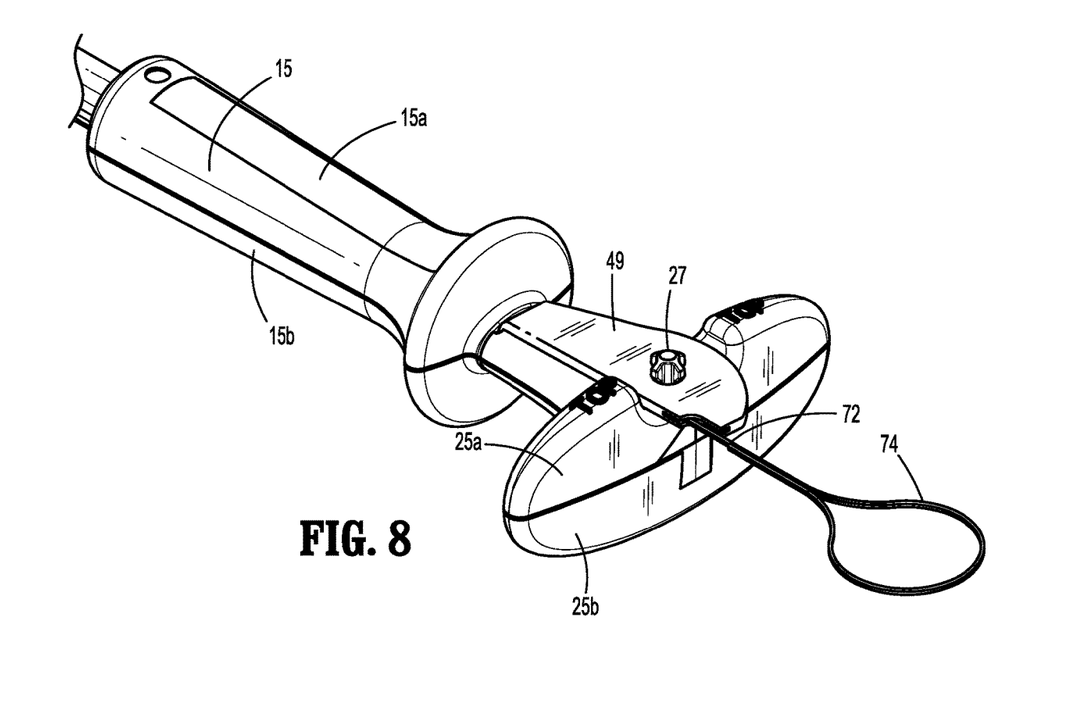
FIG. 8 is an enlarged perspective view of a proximal portion of the specimen retrieval device shown in FIG. 1 with an actuation handle in an advanced position.
Figure 9:
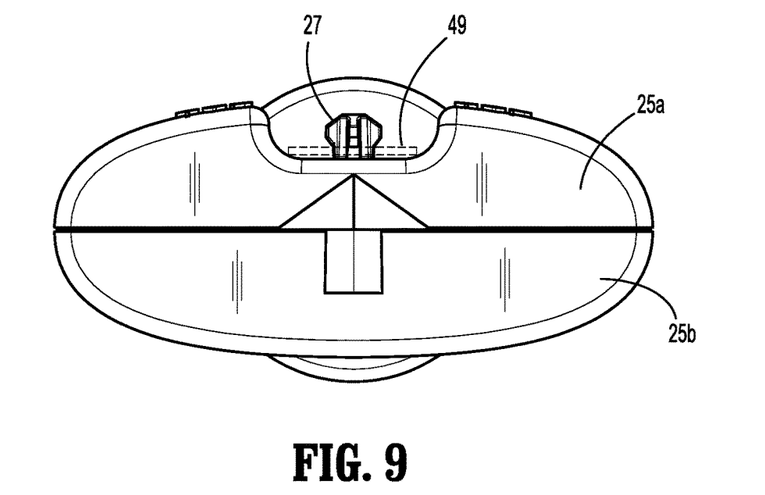
FIG. 9 is a distal view of the actuation handle of the specimen retrieval device shown in FIG. 8.
Figure 10:
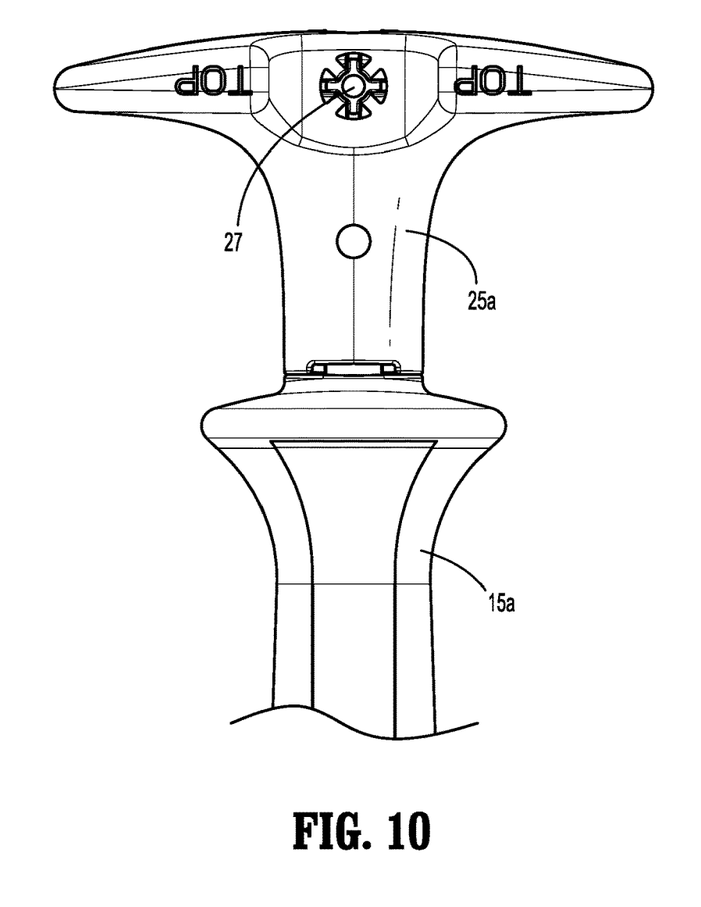
FIG. 10 is a top view of the actuation handle and a hand grip of the specimen retrieval device shown in FIG. 1.

As depicted in FIGS. 7-10, in embodiments, the actuation handle 25 at the proximal portion 24 of the inner shaft 22 has a post 27 for attaching specimen bag 40 to the actuation handle 25 (instead of carabiner types of attachments that are used by other commercially available devices), by placing the post 27 on actuation handle 25 through a hole 62 at a proximal portion 49 of the tail 48 of the specimen bag 40 (FIG. 7). The use of the post and hole configuration for attaching the tail 48 of the specimen bag 40 to the actuation handle 25 allows for easy and simple removal of the specimen bag 40 from the actuation handle 25. In addition, the design permits a more ergonomic shape for the actuation handle 25, enhancing the deployment and retraction of the specimen bag 40 from the actuation handle 25.

In embodiments, as depicted in FIGS. 7-10, the post 27 is chamfered, which allows the hole 62 at the tail 48 of the specimen bag 40 to flex over and stay secured to the post 27 until it is ready to be removed.

Referring to FIG. 6, the distal portion 26 of the inner shaft 22 is coupled to a support member 28 that is configured to support the mouth 42 of the specimen bag 40. In embodiments, the support member 28 includes a pair of resilient fingers 30, 32 that extend distally from the distal portion 26 of the inner shaft 22. In embodiments, the resilient fingers 30, 32 can be integrally formed with the distal portion 26 of the inner shaft 22 such as by molding. Alternatively, a retention pin (not shown) may be used to attach the resilient fingers 30, 32 to the distal portion 26 of the inner shaft 22. The resilient fingers 30, 32 are movable from a spaced non-deformed state (not shown) to a deformed state (FIG. 1) to facilitate placement of the specimen bag 40 into the tubular body 12.

The resilient fingers 30, 32 return to the non-deformed state when the specimen bag 40 is deployed from the tubular body 12 to open the opening 42 of the specimen bag 40, as described below.

In an assembled configuration, the hand grip 15 and the actuation handle 25 can be manipulated to facilitate manipulation of the specimen retrieval device 10 and the sliding of the inner shaft 22 within the tubular body 12. More specifically, the hand grip 15 can be grasped by the clinician with one hand and the actuation handle 25 can be grasped by the clinician with the other hand to move the inner shaft 22 within the tubular body 12.

The tubular body 12 and/or the inner shaft assembly 22 of the present disclosure are made of biocompatible materials within the purview of those skilled in the art, in embodiments, polymeric materials. For example, the tubular body 12 and/or the inner shaft assembly 22 may be made of polycarbonates or thermoplastic polyurethanes sold under the name PELLETHANE®, which offer flexibility and a wide range of hardness. The tubular body 12 and/or the inner shaft assembly 22, for example, may be fabricated from PELLETHANE® 2363-80A, PELLETHANE® 2363-90A, PELLETHANE® 2363-55D, any combination thereof, or any alternatives within the purview of those skilled in the art.

In embodiments, the tubular body 12 is made of a polymeric material combined with a lubricious material. Examples of suitable lubricious material include hydrophilic polymers, siloxanes, polycarbonates, urethanes, and/or parylenes, among other lubricious materials within the purview of those skilled in the art. In embodiments, a siloxane may be used as the lubricious material. Suitable siloxanes include, but are not limited to, polydimethylsiloxanes, hexamethyldisiloxanes, polyester-modified methylphenyl polysiloxanes, combinations thereof, and the like. In other embodiments, a combination of a siloxane and a polycarbonate may be used to form the tubular body 12.

For example, in some embodiments, the tubular body is made of a blend of a polycarbonate with a siloxane, which is extruded into the form of the tubular body. The siloxane improves lubricity for the passage of the inner shaft assembly and the specimen bag through the outer tube to deploy the specimen bag in the patient's body.

In some embodiments, the tubular body 12 and the inner shaft assembly 22 are formed of the same material. In other embodiments, the tubular body 12 and the inner shaft assembly 22 are formed of different materials.

In embodiments, the mouth 42 of the specimen bag 40 has a pull string 70 attached thereto (FIG. 11), as well as resilient fingers 30, 32 attached thereto. In other embodiments, the resilient fingers 30, 32 and the pull string 70 may be received in the cuff 43 formed at the mouth 42 of the specimen bag 40.

In use, the tubular body 12 of the specimen retrieval device 10 can be inserted through an incision (not shown) with the specimen bag 40 furled about the inner shaft 22 and positioned within the tubular body 12 to position the specimen bag 40 in a body cavity adjacent a surgical site. When the tubular body 12 is properly positioned, the clinician can grip the hand grip 15.

Figure 11:
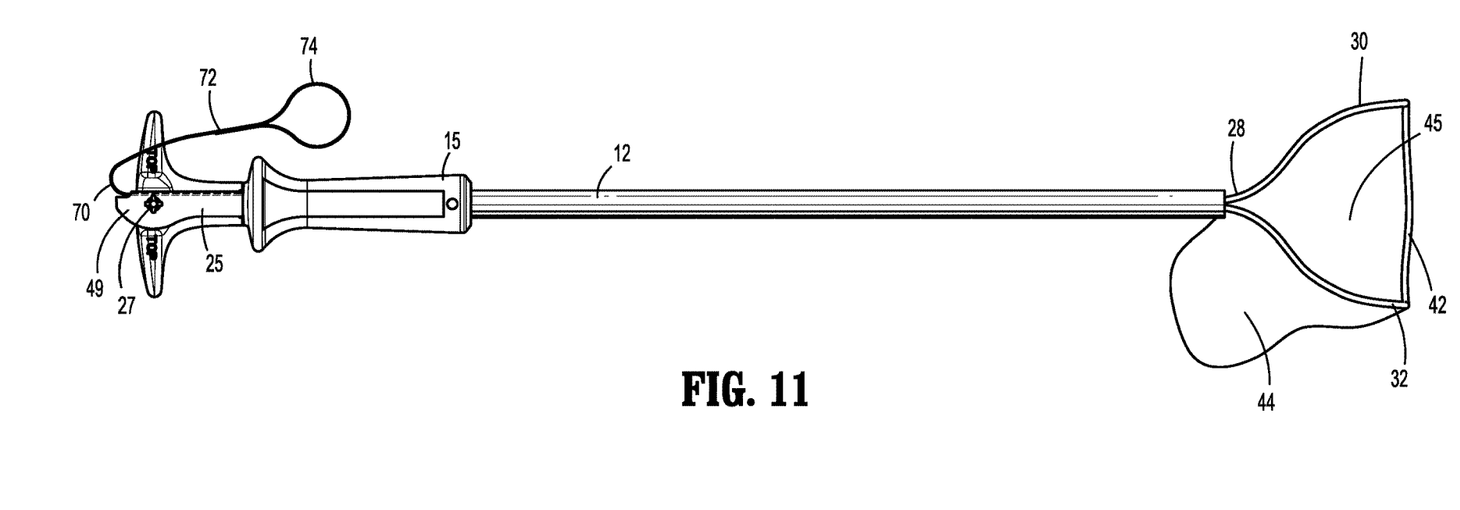
FIG. 11 is a top view of the specimen retrieval device shown in FIG. 1.

The clinician then pushes the actuation handle 25 on the proximal portion 24 of the inner shaft 22 distally in relation to the hand grip 15 and the tubular body 12 (not shown), so the distal portion 26 of the inner shaft 22, including the specimen bag 40, exits the distal portion 18 of the tubular body 12 (FIG. 1). Once the specimen bag 40 has exited the tubular body 12, the resilient fingers 30, 32 (FIG. 4) return to their non-deformed state, thereby opening the mouth 42 of the specimen bag 40 to ensure the specimen bag 40 is deployed (FIG. 11).

Figure 12:
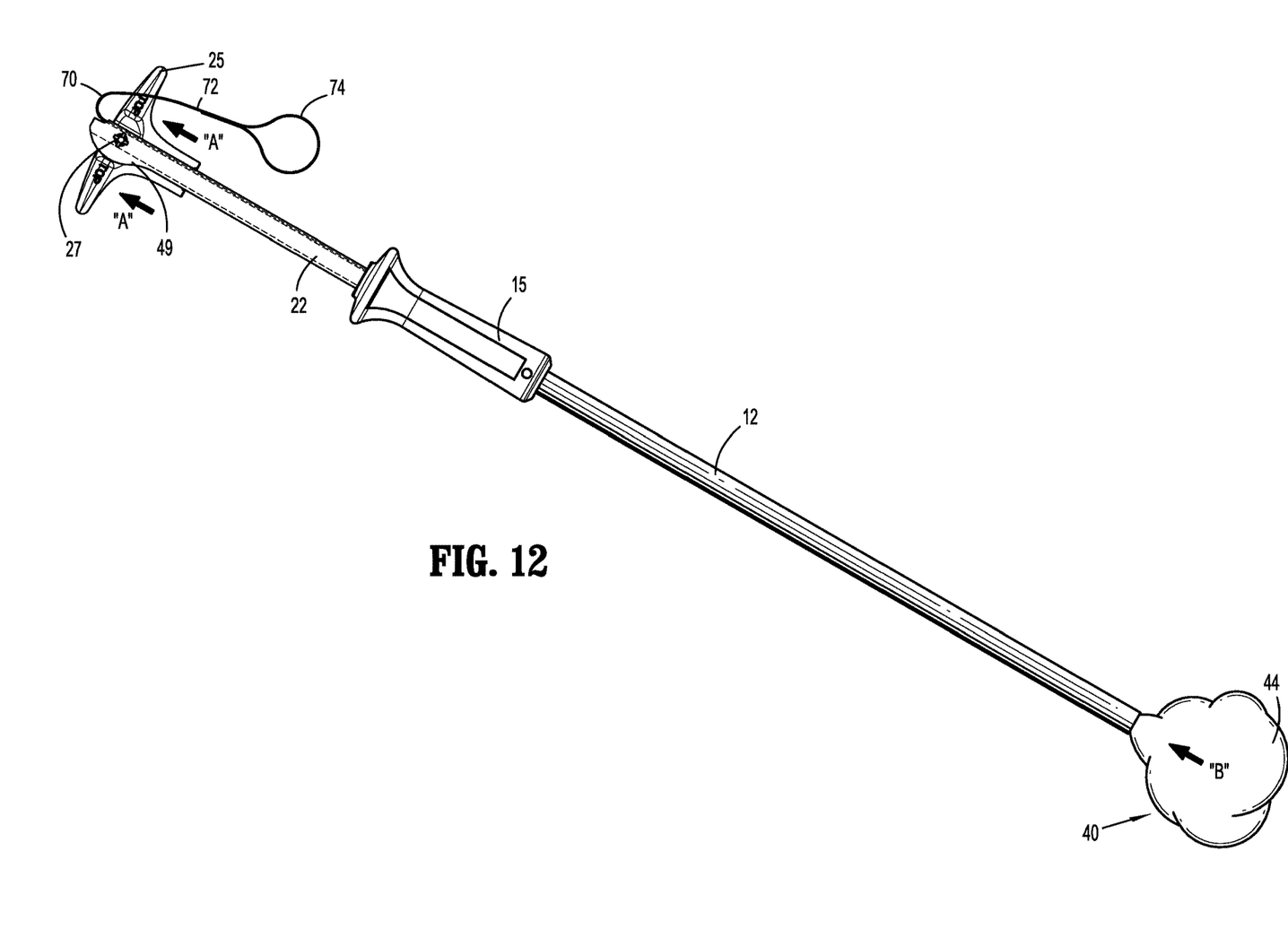
FIG. 12 is a top view of the specimen retrieval device shown in FIG. 11, depicting the withdrawal of the specimen bag into the tubular body of the specimen retrieval device.

As depicted in FIG. 12, after a tissue specimen (not shown) has been placed in the specimen bag 40, the pull string 70 is pulled proximally (indicated by arrows "A" in FIG. 12) to pull the pull string 70 proximally, thus cinching the mouth 42 of the specimen bag 40 closing the opening 42, and withdrawing a portion of the specimen bag 40 into the inner shaft 12 (indicated by arrow "B" in FIG. 12). As depicted in FIG. 12, the proximal portion 72 of the pull string 70 may be in the form of a loop 74 that may assist in pulling the pull string 70.

Kits of the present disclosure may include both the specimen retrieval device described above, as well as trocars, graspers, vacuum sources (tubes), combinations thereof, and the like. In some embodiments, these additional devices, such as graspers and/or vacuum sources, may be used to break up the tissue specimen in the specimen bag prior to removing the specimen retrieval device from the body cavity.

Once the specimen retrieval device of the present disclosure has been removed from the patient's body, any tissue specimen may be removed from the specimen bag 40 for further examination and the specimen bag 40 may be discarded.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A specimen retrieval device comprising:
   a tubular body defining a longitudinal bore, the tubular body having a proximal portion, a distal portion, and a hand grip supported on the proximal portion of the tubular body;
   an inner shaft having a proximal portion, a distal portion, an actuation handle supported on the proximal portion of the inner shaft, and a support member extending from the distal portion of the inner shaft; and
   a specimen bag supported on the support member at the distal portion of the inner shaft, the specimen bag including an open end, a body, and a tail portion having an enclosed longitudinal bore through which the inner shaft passes,
   wherein the inner shaft is movable in relation to the tubular body from a non-actuated position in which the specimen bag is positioned in a non-deployed state within the longitudinal bore of the tubular body to an actuated position in which the specimen bag is positioned in a deployed state externally of the distal portion of the tubular body.

2. The specimen retrieval device of claim 1, wherein a proximal portion of the tail portion of the specimen bag has a hole, and the actuation handle includes a post which passes through the hole at the proximal portion of the tail portion of the specimen bag.

3. The specimen retrieval device of claim 2, wherein the post is chamfered.

4. The specimen retrieval device of claim 1, wherein the support member includes a pair of resilient fingers which support the specimen bag and open the open end of the specimen bag in the deployed state.

5. The specimen retrieval device of claim 4, wherein the resilient fingers are positioned adjacent the open end of the specimen bag to open the specimen bag when the specimen retrieval device is in the deployed state.

6. The specimen retrieval device of claim 1, wherein the tubular body is formed of a lubricious material.

7. The specimen retrieval device of claim 6, wherein the tubular body includes a polymeric material combined with the lubricious material.

8. The specimen retrieval device of claim 7, wherein the lubricious material includes hydrophilic polymers, siloxanes, polycarbonates, urethanes, parylenes, or combinations thereof.

9. The specimen retrieval device of claim 7, wherein the lubricious material includes a siloxane selected from polydimethylsiloxanes, hexamethyldisiloxanes, polyester-modified methylphenyl polysiloxanes, or combinations thereof.

10. The specimen retrieval device of claim 7, wherein the tubular body is formed of a combination of a siloxane and a polycarbonate.

11. The specimen retrieval device of claim 1, wherein the tail portion of the specimen bag includes a reinforcement tab.

* * * * *